United States Patent [19]

An Haack

[11] Patent Number: 5,377,695
[45] Date of Patent: Jan. 3, 1995

[54] WOUND-CLOSING STRIP

[76] Inventor: Karl W. An Haack, Am Hedreisch 25, D-44225 Dortmund, Germany

[21] Appl. No.: 218,327

[22] Filed: Mar. 25, 1994

[30] Foreign Application Priority Data

Jan. 13, 1994 [DE] Germany ............... 4400732

[51] Int. Cl.⁶ .................. A61F 13/00; A61B 17/08
[52] U.S. Cl. ..................... 128/888; 606/213; 606/216; 606/217
[58] Field of Search ............... 128/888, 889, 849–856, 128/894; 606/213–217

[56] References Cited

U.S. PATENT DOCUMENTS

| | | |
|---|---|---|
| 1,428,495 | 9/1922 | Radcliffe ............... 606/216 |
| 1,774,489 | 8/1930 | Sarason ............... 606/216 |
| 2,012,755 | 8/1935 | De Muth . | 
| 2,752,921 | 7/1956 | Fink ............... 606/217 |
| 2,873,741 | 2/1959 | Donaldson ............... 606/217 |
| 3,516,409 | 6/1970 | Howell . |
| 3,568,276 | 3/1971 | Morgan ............... 606/217 |
| 4,881,546 | 11/1989 | Kaessmann . |
| 4,905,694 | 3/1990 | Will ............... 606/217 |

*Primary Examiner*—Michael A. Brown
*Attorney, Agent, or Firm*—Herbert Dubno; Andrew Wilford

[57] ABSTRACT

A closure for an elongated skin wound having a pair of edges has a pair of parallel tapes each formed by a U-shaped one-piece textile outer strip having a longitudinally extending outside flap and, parallel thereto, an inside flap joined at a longitudinal fold, and a filler strip extending longitudinally between and spacing the flaps apart. Each tape has an inner edge turned toward the other tape and carrying one of a pair of longitudinal rows of interleavable teeth on the outside flaps. Stitches or the like engaged through the flaps and filler strip of each tape hold them together. A skin-compatible adhesive adhered to inside faces of the inside flaps allows the inside flaps to be adhered to skin to each side of the wound. A slider displaceable longitudinally along the rows of teeth can interleave and couple them together so that, when the tapes are adhered to skin to each side of the wound, coupling the rows of teeth with the slider pulls the edges of the wound together.

10 Claims, 3 Drawing Sheets

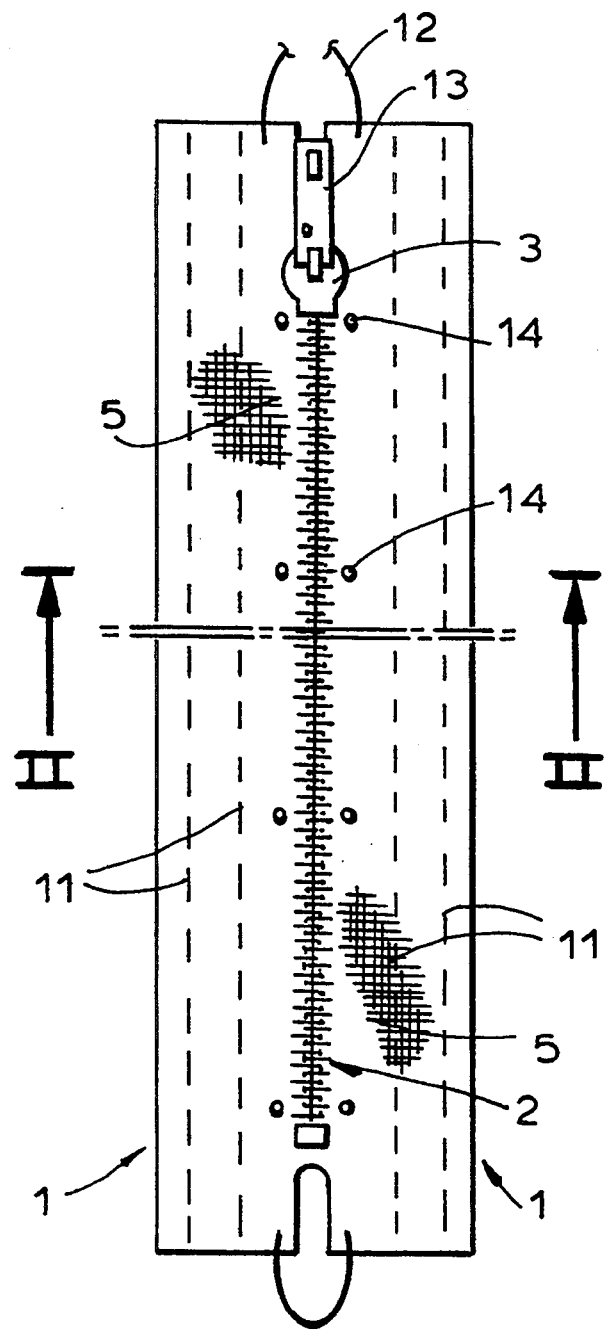
F I G. 1

WOUND-CLOSING STRIP

FIELD OF THE INVENTION

The present invention relates to a wound-closing strip. More particularly this invention concerns a strip specifically intended to pull together the edges of a straight surgical incision.

BACKGROUND OF THE INVENTION

A typical such closure comprises a slide fastener consisting of two textile support tapes carrying rows of interleavable coupling members that can be joined by a slider. The tapes are adhered to the patient's skin to either side of the wound or incision with the slider down and the teeth not coupled, then the slider is drawn up to pull the lips of the wound together. Thus this closure is not intended to cover the wound, but instead serves to pull the sides of the injury together so that they can knit and heal. Although it is used most easily on a straight surgical incision, it can also be applied to S-shaped or curved wounds, lacerations, contused wounds, and the like.

Such a system is described in U.S. Pat. No. 4,881,546 of H Kaessmann. In it the slide fastener is a conventional flexible fastener of the kind used for textile garments, insofar as concerns the rows of coupling members and the support tapes which are of low elasticity and the rows of coupling members which consist of polyester or polyamide and are resistant to compression in the closed state. Spacer strips which form a wound-space zone are disposed on the support tapes at a spacing from the rows of coupling members, on the under side facing the wound. The adhesive connection is made by adhesive strips connected to the support tapes and projecting therefrom. These strips have a skin-compatible adhesive coating on the skin side. The support tapes are backed by the adhesive strip over at least part of their width. The adhesive strips including the projections have a width suitable for taking the transverse tensile forces in the case of the wound being closed by the slide fastener and having abutting wound edges, i.e. the wound edges are pressed against one another. The known device has proved satisfactory and meets all requirements medically, but in terms of manufacture it is expensive, a feature which is particularly disturbing inasmuch as these devices are mass-production products.

OBJECTS OF THE INVENTION

It is therefore an object of the present invention to provide an improved wound closure.

Another object is the provision of such an improved wound closure which overcomes the above-given disadvantages, that is which is easy to use and safe and which is cheap to manufacture.

SUMMARY OF THE INVENTION

A closure for an elongated skin wound having a pair of edges has according to the invention a pair of parallel tapes each formed by a U-shaped one-piece textile outer strip having a longitudinally extending outside flap and, parallel thereto, an inside flap joined at a longitudinal fold, and a filler strip extending longitudinally between and spacing the flaps apart. Each tape has an inner edge turned toward the other tape and carrying one of a pair of longitudinal rows of interleavable teeth on the outside flaps. Stitches or the like engaged through the flaps and filler strip of each tape hold them together. A skin-compatible adhesive adhered to inside faces of the inside flaps allows the inside flaps to be adhered to skin to each side of the wound. A slider displaceable longitudinally along the rows of teeth can interleave and couple them together so that, when the tapes are adhered to skin to each side of the wound, coupling the rows of teeth with the slider pulls the edges of the wound together.

The invention is based on the realization that a conventional sliding clasp fastener can, without difficulty and without undue modification of production technique, be provided with support tapes of a sufficient width directly or indirectly provided with an adhesive to be able to take the transverse tensile forces occurring during the closing of the sliding clasp fastener, when a wound is closed. To this end the invention makes use of slide fasteners whose support tapes are arranged in the manner described, i.e. slide fasteners which can be manufactured without difficulty using conventional slide-fastener production equipment. Appropriate automatic tape weaving or knitting machines are extensively known and have proved satisfactory. The other steps required to make the device according to the invention from this product in the form of a slide fastener are simple and can be produced easily both manually and automatically.

In order to provide sufficient grip, the flaps are of generally the same transverse width of a few centimeters. More specifically, substantially the entire inside face of each flap is covered with the adhesive. In addition the filler strip has a width substantially equal to a width of the flaps and is of textile construction.

The adhesive can be carried directly on the inside face of the inside flap, or it can be on a respective mounting strip secured to each inside face by the securer and itself having an inside face carrying the adhesive. This mounting strip is substantially wider than the inside flap and projects outward therepast when additional hold is needed. In accordance with a further feature of the invention tapes are each secured together by is stitching engaged through the flaps, mounting strip, and filler strip.

BRIEF DESCRIPTION OF THE DRAWING

The above and other objects, features, and advantages will become more readily apparent from the following description, it being understood that any feature described with reference to one embodiment of the invention can be used where possible with any other embodiment and that reference numerals or letters not specifically mentioned with reference to one figure but identical to those of another refer to structure that is functionally if not structurally identical. In the accompanying drawing:

FIG. 1 is a top view of the wound closure according to the invention in the closed position;

SPECIFIC DESCRIPTION

Figure 2:
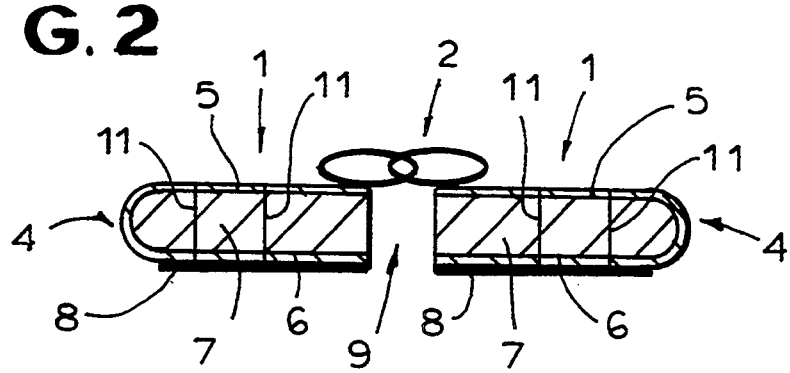
FIG. 2 is a section taken along line II—II of FIG. 1.
Figure 6:
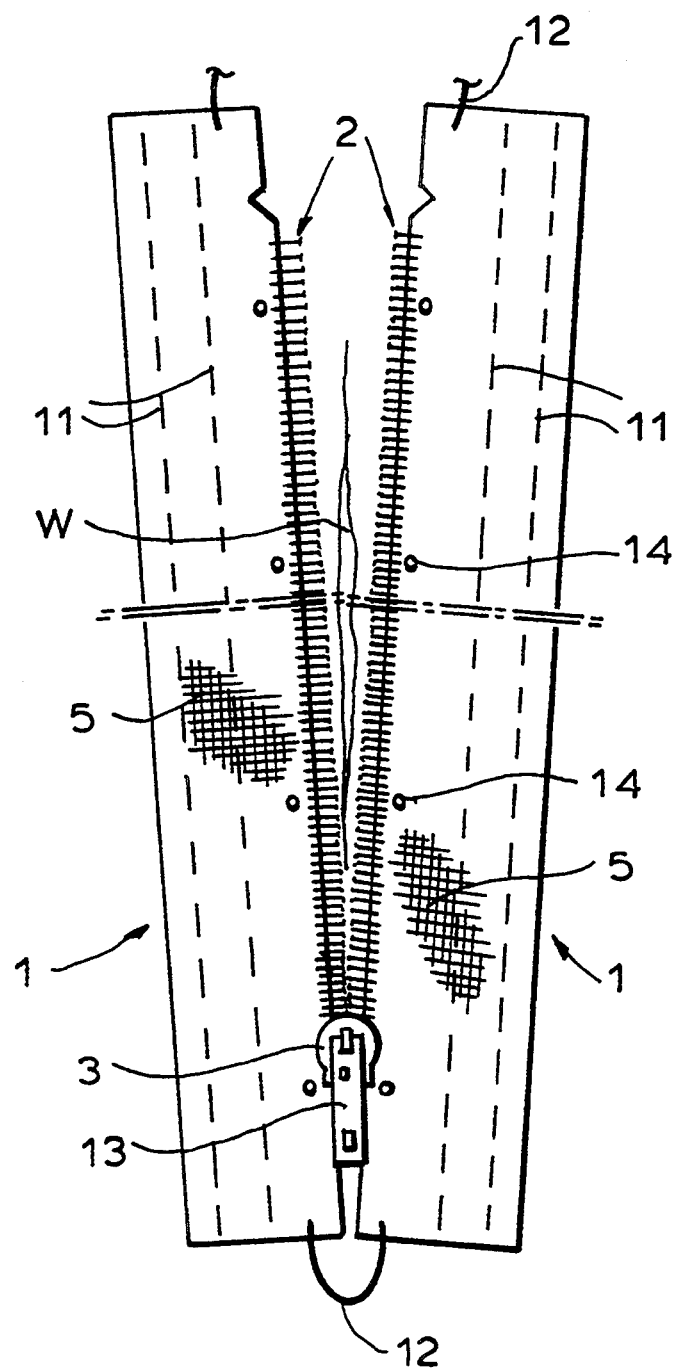
FIG. 6 is a top view of the wound closure of FIG. 1 in the open position.

As seen in FIGS. 1, 2, and 6 the instant invention is used to close a generally straight wound W, here a surgical incision. It is basically formed as a slide fastener having a pair of tapes 1 having confronting inner edges provided with rows of coupling members or teeth 2 that can be joined or interleaved by a standard slider 3 having a pull tab 13. As is known in the art the fastener is normally adhered to the patient's skin in the region where the incision W is to be made, then is opened and the operation progresses as normally. When completed, the fastener is closed from the FIG. 6 to the FIG. 1 position by longitudinal movement of the slider 3 the full length of the teeth rows 2 to draw the edges of the wound W together.

A comparison of FIGS. 2 to 5, in particular, will show that the support tapes 1 of the slide fastener are of U- or C-section and are each folded over at a longitudinal fold 4 at the outer edge of the respective tape to form an outside flap 5 connected to the respective rows 2 of coupling members and a inside flap 6 parallel to the outside flap 5. A spacer strip 7 which forms a wound-clearing space is disposed between each tape flap 6 and the tape flap 5 connected to the rows 2 of coupling members. A skin-compatible or hypoallergenic adhesive 8 is applied directly or indirectly to the lower or inside exposed face of the tape flap 6. The arrangement is such that the support tape flap 5 connected to the rows of coupling members 2, the flap 6, and the spacer strip 7 are joined together in the double tape zone.

The fastener support tapes 1 may each have a rectified, that is when flattened out, width of several centimeters, the longitudinal fold 4 being in the middle of the width. If considerable transverse tensile forces have to be withstood, the flap 6 provided with the adhesive 8 will have a width of several centimeters.

The spacer strips 7, which form a wound-clearing space and which, more particularly, must be operative in the area of the wound W, have substantially the width of the half of the tape 1 as shown in the drawings. They are constructed as textile inserts and may be woven, knitted, or be made as non-woven strips of adequate density.

Figure 3:
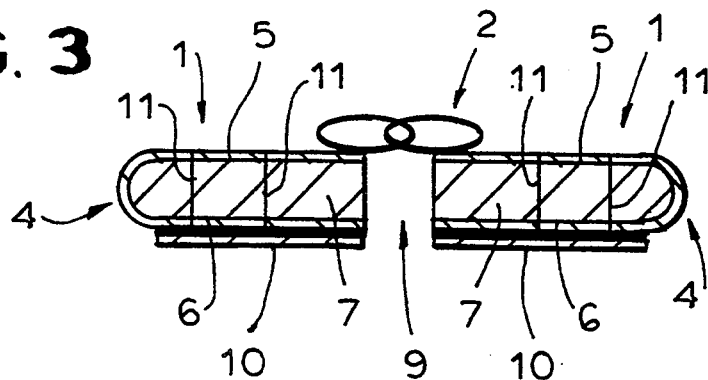
FIGS. 3, 4, and 5 are views like FIG. 2 of other closures according to the invention.
Figure 4:
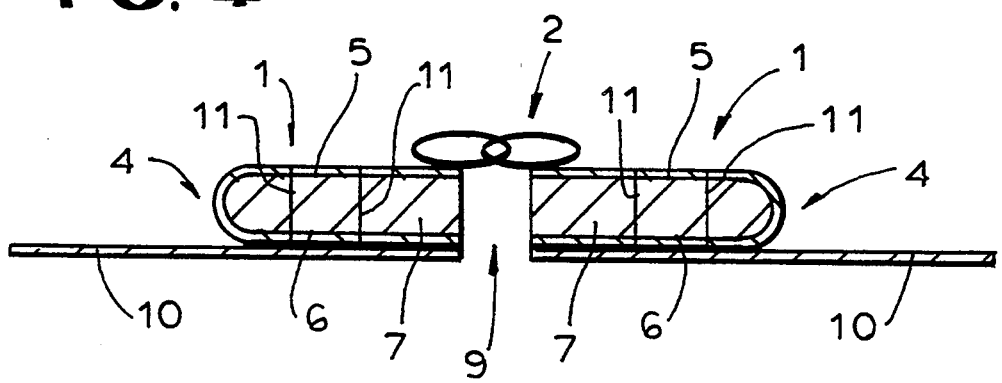
Figure 5:
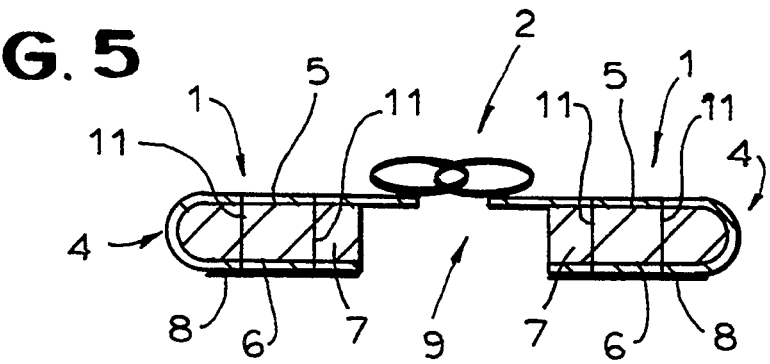

According to a preferred embodiment of the invention, the skin-compatible adhesive 8 is of the type used on medical adhesive tape or the plastic strips of the BandAid TM type and is applied directly to the exposed surface of the turned-in tape flap 6. In this connection see FIGS. 2 and 5. A comparison of these two figures will show that the wound-clearing area 9 may vary in width, the only essential feature being that the turned-in tape flap 6 and the spacer strip 7 should be wider or less wide. The skin-compatible adhesive 8 can also be applied to an adhesive plaster adhesive strip 10. In this connection see FIGS. 3 and 4. It will be seen that the adhesive plaster adhesive strip 10 is applied against the exposed surface of the turned-in tape flap 6 and is connected to the latter. When very considerable transverse tensile forces have to be taken, the arrangement can without difficulty be such that the adhesive plaster adhesive strip 10 projects beyond the turned-in tape strip 4 on each side of the fastener, at that side which is remote from the coupling member rows 2. This is shown in FIG. 4. The width of the projection depends on the tensile stresses to be withstood.

The drawings show that the support tape strips 1, the spacer strip 7 forming the wound-clearing area, and the turned-in tape flap 6 are joined together in the double tape zone by sewn and/or tacked seams 11. In the embodiment with adhesive plaster adhesive tape 10 the support tape strips 1, the spacer strip 7 forming the wound-clearing area, the turned-in tape flap 6, and the adhesive plaster adhesive tapes 10 will be interconnected in the double tape zone by sewn or tacked seams 11 as shown in FIGS. 3 and 4. FIGS. 1 and 6 show that holding loops 12 are connected to the beginning and the end of the support tapes 1. When the fastener is closed, an operation during which the edges of the initially gaping wound W are drawn together to abut at the same level, the operator holds the pull tab 13 of the slider 3 in one hand and the loop 12 at the closed end of the fastener in the other hand. The slider 3 is moved until the fastener is completely closed, the wound edges being drawn together as described. If the fastener is opened, then conversely the loop 12 at the open end of the fastener will be held fast and the slider 3 moved in the opening direction. This may be necessary, for example, to inspect the healing process at the wound W. In any case, the loops 12 can be used to ensure that the tensile forces which occur when the fastener is closed or re-opened by means of the slider 3 do not have to be taken by the patient's skin via the adhesive 8, but, on the contrary, by the operator's hands, which on the one hand engage the slider 3 and, on the other hand, the loop 12 arranged to take the tensile forces. Of course, the fastener support tapes 1, the spacer strip 7 forming the wound-clearing area, and where applicable the adhesive 8 or adhesive plaster tapes 10 may have ventilation apertures 14 in the form of perforations.

I claim:

1. A closure for an elongated skin wound having a pair of edges, the closure comprising:
   a pair of parallel tapes each formed by
      a U-shaped one-piece textile outer strip having a longitudinally extending outside flap and, parallel thereto, an inside flap joined at a longitudinal fold, inner edges, and
      a filler strip extending longitudinally between and spacing the flaps apart,
   respective longitudinal rows of interleavable teeth on the outside flaps at the inner edges of the tapes;
   respective securing means engaged through the flaps and filler strip of each tape for holding them together;
   a skin-compatible adhesive adhered to inside faces of the inside flaps, whereby the inside flaps can be adhered to skin to each side of the wound;
   a slider displaceable longitudinally along the rows of teeth to interleave and couple them together, whereby, when the tapes are adhered to skin to each side of the wound, coupling the rows of teeth with the slider pulls the edges of the wound together.

2. The wound closure defined in claim 1 wherein the flaps are of generally the same transverse width.

3. The wound closure defined in claim 1 wherein substantially the entire inside face of each flap is covered with the adhesive.

4. The wound closure defined in claim 1 wherein the filler strip has a width substantially equal to a width of the flaps and is of textile construction.

5. The wound closure defined in claim 1 wherein the adhesive is carried directly on the inside face of the inside flap.

6. The wound closure defined in claim 1, further comprising
   a respective mounting strip secured to each inside face by the securing means and itself having an inside face carrying the adhesive.

7. The wound closure defined in claim 6 wherein the mounting strip is substantially wider than the inside flap and projects outward therepast.

8. The wound closure defined in claim 7 wherein the securing means is stitching engaged through the flaps, mounting strip, and filler strip.

9. The wound closure defined in claim 1 wherein the securing means is stitching engaged through the flaps and filler strip.

10. The wound closure defined in claim 1, further comprising gripping formations at each longitudinal end of the tapes.

* * * * *